United States Patent
Zhang et al.

(10) Patent No.: US 11,125,894 B2
(45) Date of Patent: Sep. 21, 2021

(54) RAY DETECTOR, METHOD FOR MANUFACTURING THE SAME AND ELECTRONIC DEVICE

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Yong Zhang, Beijing (CN); Yanna Xue, Beijing (CN); Haobo Fang, Beijing (CN); Lu Bai, Beijing (CN); Gang Hua, Beijing (CN); Limin Zhang, Beijing (CN); Jian Lin, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 20 days.

(21) Appl. No.: 16/647,281

(22) PCT Filed: Oct. 8, 2019

(86) PCT No.: PCT/CN2019/109893
§ 371 (c)(1),
(2) Date: Mar. 13, 2020

(87) PCT Pub. No.: WO2020/103583
PCT Pub. Date: May 28, 2020

(65) Prior Publication Data
US 2021/0215835 A1   Jul. 15, 2021

(30) Foreign Application Priority Data

Nov. 21, 2018  (CN) .......................... 201811392902.9
Sep. 20, 2019  (CN) .......................... 201910894639.1

(51) Int. Cl.
*G01T 1/20* (2006.01)
*H01L 27/146* (2006.01)

(52) U.S. Cl.
CPC ...... *G01T 1/2018* (2013.01); *H01L 27/14623* (2013.01); *H01L 27/14663* (2013.01); *H01L 27/14685* (2013.01); *H01L 27/14689* (2013.01)

(58) Field of Classification Search
CPC ............ G01T 1/2018; H01L 27/14623; H01L 27/14663; H01L 27/14685; H01L 27/14689
See application file for complete search history.

(56) References Cited

U.S. PATENT DOCUMENTS

| 4,996,573 | A | * | 2/1991 | Hack | .................... H01L 27/1443 |
| | | | | | 257/401 |
| 6,044,128 | A | * | 3/2000 | Tanaka | .................. G01T 1/2928 |
| | | | | | 250/370.09 |

(Continued)

FOREIGN PATENT DOCUMENTS

| CN | 1778102 A | 5/2006 |
| CN | 105336751 A | 2/2016 |

(Continued)

*Primary Examiner* — Blake C Riddick
(74) *Attorney, Agent, or Firm* — Myers Bigel, P.A.

(57) ABSTRACT

A ray detector includes a base substrate including a plurality of pixel regions arranged in an array. Each pixel region includes a thin film transistor including a source and a drain, and a photoelectric sensor on the thin film transistor. The photoelectric sensor includes a first electrode and a second electrode spaced apart from each other, a dielectric layer on the first electrode and the second electrode and covering the first electrode and the second electrode, and a first semiconductor layer on the dielectric layer. The first electrode is electrically connected to the drain. A distance between a surface of the first electrode away from the base substrate (Continued)

and the base substrate is a first distance. A distance between a surface of the second electrode away from the base substrate and the base substrate is a second distance. The first distance is substantially equal to the second distance.

18 Claims, 3 Drawing Sheets

(56) References Cited

U.S. PATENT DOCUMENTS

| | | | | |
|---|---|---|---|---|
| 6,163,386 | A * | 12/2000 | Kobayashi | H04N 5/3454 348/304 |
| 6,185,274 | B1 * | 2/2001 | Kinno | G01T 1/2928 250/370.07 |
| 6,225,632 | B1 * | 5/2001 | Kinno | H01L 27/14603 250/370.09 |
| 6,323,490 | B1 * | 11/2001 | Ikeda | H01L 27/14659 250/370.07 |
| 6,690,493 | B1 * | 2/2004 | Kobayashi | H04N 5/3454 348/307 |
| 2006/0077308 | A1 * | 4/2006 | Mochizuki | H01L 27/14663 348/800 |
| 2006/0192130 | A1 | 8/2006 | Yagi | |
| 2006/0289769 | A1 * | 12/2006 | Yagi | G01T 1/24 250/362 |
| 2008/0036881 | A1 * | 2/2008 | Kobayashi | H04N 5/3577 348/241 |
| 2013/0099093 | A1 * | 4/2013 | Kawanabe | H01L 27/14609 250/208.1 |
| 2016/0049431 | A1 * | 2/2016 | Taghibakhsh | H01L 27/14638 250/370.08 |
| 2018/0151742 | A1 | 5/2018 | Kurata et al. | |
| 2018/0315792 | A1 * | 11/2018 | Sekine | H01L 27/14663 |
| 2018/0341031 | A1 * | 11/2018 | Tredwell | H04N 5/3745 |

FOREIGN PATENT DOCUMENTS

| | | |
|---|---|---|
| CN | 108646283 | 10/2018 |
| CN | 109276268 A | 1/2019 |
| JP | 2013-41944 A | 2/2013 |

* cited by examiner

RAY DETECTOR, METHOD FOR MANUFACTURING THE SAME AND ELECTRONIC DEVICE

RELATED APPLICATIONS

The present application is a 35 U.S.C. 371 national stage application of PCT International Application No. PCT/CN2019/109893, filed on Oct. 8, 2019, which claims the benefit of Chinese Patent Application No. 201811392902.9, filed on Nov. 21, 2018, and the benefit of Chinese Patent Application No. 201910894639.1, filed on Sep. 20, 2019, the entire disclosures of which are incorporated herein by reference.

TECHNICAL FIELD

The present disclosure relates to the field of sensing technologies, and in particular, to a ray detector, a method for manufacturing the ray detector, and an electronic device including the ray detector.

BACKGROUND

In the medical field, when an X-ray is taken on a part to be diagnosed of a human body, an X-ray emitter and an X-ray detector are placed opposite to each other, and the part to be diagnosed is placed between the X-ray emitter and the X-ray detector. The X-ray emitter emits X-rays to the part to be diagnosed. The X-ray detector receives X-rays transmitted from the part to be diagnosed and converts the X-rays into visible light. The photodiode in the X-ray detector then converts the visible light into an electrical signal and sends the electrical signal to a signal reading circuit. An image frame can be formed according to the electrical signal read by the signal reading circuit.

Currently, X-ray detectors typically use PIN photodiodes or metal-semiconductor-metal (MSM) photodiodes. Compared with PIN photodiodes, MSM photodiodes have a larger fill rate and a faster response speed, and have better compatibility with a-Si thin film transistors, so they are increasingly used in X-ray detector.

SUMMARY

According to some embodiments of the present disclosure, there is provided a ray detector including a base substrate. A plurality of pixel regions are arranged in an array on the base substrate. Each pixel region of the plurality of pixel regions includes a thin film transistor and a photoelectric sensor on a side of the thin film transistor away from the base substrate. The thin film transistor includes a source and a drain. The photoelectric sensor includes: a first electrode and a second electrode spaced apart from each other; a dielectric layer on a side of the first electrode and the second electrode away from the base substrate and covering the first electrode and the second electrode; and a first semiconductor layer on a side of the dielectric layer away from the base substrate. The first electrode is electrically connected to the drain. A distance between a surface of the first electrode away from the base substrate and the base substrate is a first distance, a distance between a surface of the second electrode away from the base substrate and the base substrate is a second distance, and the first distance is substantially equal to the second distance.

In some embodiments, the ray detector further includes: a first insulating layer between the dielectric layer and the base substrate; a second insulating layer between the first insulating layer and the dielectric layer; and a shielding layer between the first insulating layer and the second insulating layer. The shielding layer includes a first portion, and an orthographic projection of the first portion on the base substrate and an orthographic projection of the second electrode on the base substrate at least partially overlap.

In some embodiments, the orthographic projection of the first portion of the shielding layer on the base substrate covers the orthographic projection of the second electrode on the base substrate.

In some embodiments, the ray detector further includes a common electrode between the base substrate and the first insulating layer. Orthographic projections of the first electrode, the drain, and the common electrode on the base substrate at least partially overlap with each other.

In some embodiments, the common electrode includes a first thickness, the drain includes a second thickness, and the first portion of the shielding layer includes a third thickness. The third thickness is substantially equal to a sum of the first thickness and the second thickness.

In some embodiments, the thin film transistor further includes a gate and a second semiconductor layer stacked on each other. The gate is between the base substrate and the first insulating layer. The second semiconductor layer is connected to the source and the drain. A portion of the second semiconductor layer between the source and the drain forms a channel region. The shielding layer further includes a second portion, and an orthographic projection of the second portion on the base substrate covers at least an orthographic projection of the channel region on the base substrate.

In some embodiments, orthographic projections of the first electrode, the second portion of the shielding layer, and the gate on the base substrate at least partially overlap with each other. The gate includes a thickness substantially equal to the first thickness. The second portion of the shielding layer includes a fourth thickness, and the fourth thickness is substantially equal to the second thickness.

In some embodiments, the ray detector further includes a gate line between the base substrate and the first insulating layer and connected to the gate. Orthographic projections of the first electrode, the second portion of the shielding layer, and the gate line on the base substrate at least partially overlap with each other. The gate line includes a thickness substantially equal to the first thickness.

In some embodiments, the common electrode and the shielding layer are electrically connected to a same common voltage signal terminal.

According to some embodiments of the present disclosure, an electronic device is provided. The electronic device includes the ray detector described in any of the foregoing embodiments.

According to some embodiments of the present disclosure, a method for manufacturing a ray detector is provided. The method includes: providing a base substrate including a plurality of pixel regions arranged in an array; forming a corresponding thin film transistor in each pixel region of the plurality of pixel regions, wherein the thin film transistor includes a source and a drain; forming a first electrode and a second electrode on a side of the thin film transistor in each pixel region away from the base substrate, wherein the first electrode and the second electrode are spaced apart from each other, and the first electrode is electrically connected to the drain; forming a dielectric layer covering the first electrode and the second electrode on a side of the first electrode and the second electrode away from the base substrate; and forming a first semiconductor layer on a side of the dielectric layer away from the base substrate. The first electrode, the second electrode, the dielectric layer, and the first semiconductor layer form a photoelectric sensor. A distance between a surface of the first electrode away from the base substrate and the base substrate is a first distance, a distance between a surface of the second electrode away from the base substrate and the base substrate is a second distance, and the first distance is substantially equal to the second distance.

In some embodiments, the method further includes: before forming the first electrode and the second electrode, forming a first insulating layer on a side of the thin film transistor away from the base substrate; forming a shielding layer on a side of the first insulating layer away from the base substrate; and forming a second insulating layer on a side of the shielding layer away from the base substrate. The shielding layer includes a first portion, and an orthographic projection of the first portion on the base substrate and an orthographic projection of the second electrode on the base substrate at least partially overlap.

In some embodiments, the orthographic projection of the first portion of the shielding layer on the base substrate covers the orthographic projection of the second electrode on the base substrate.

In some embodiments, the method further includes: forming a common electrode between the base substrate and the first insulating layer. Orthographic projections of the first electrode, the drain, and the common electrode on the base substrate at least partially overlap with each other.

In some embodiments, the common electrode includes a first thickness, the drain includes a second thickness, and the first portion of the shielding layer includes a third thickness. The third thickness is substantially equal to a sum of the first thickness and the second thickness.

In some embodiments, forming the corresponding thin film transistor in each pixel region includes: forming a gate and a second semiconductor layer stacked on each other. The gate is between the base substrate and the first insulating layer, the second semiconductor layer is connected to the source and the drain, and a portion of the second semiconductor layer between the source and the drain forms a channel region. Forming the shielding layer includes: forming a second portion of the shielding layer. An orthographic projection of the second portion on the base substrate covers at least an orthographic projection of the channel region on the base substrate.

In some embodiments, orthographic projections of the first electrode, the second portion of the shielding layer, and the gate on the base substrate at least partially overlap with each other. The gate includes a thickness substantially equal to the first thickness, the second portion of the shielding layer includes a fourth thickness, and the fourth thickness is substantially equal to the second thickness.

In some embodiments, the method further includes: forming a gate line between the base substrate and the first insulating layer. The gate line is connected to the gate. Orthographic projections of the first electrode, the second portion of the shielding layer, and the gate line on the base substrate at least partially overlap with each other. The gate line includes a thickness substantially equal to the first thickness.

BRIEF DESCRIPTION OF THE DRAWINGS

Embodiments of the present disclosure will be further described below in a non-limiting manner and with reference to the accompanying drawings, in which.

In the drawings, the same reference numerals in various drawings generally refer to the same or similar parts. Moreover, the drawings are not necessarily drawn to scale, emphasis instead generally being placed upon illustrating the principles of the present disclosure.

DETAILED DESCRIPTION OF THE DISCLOSURE

Figure 1:
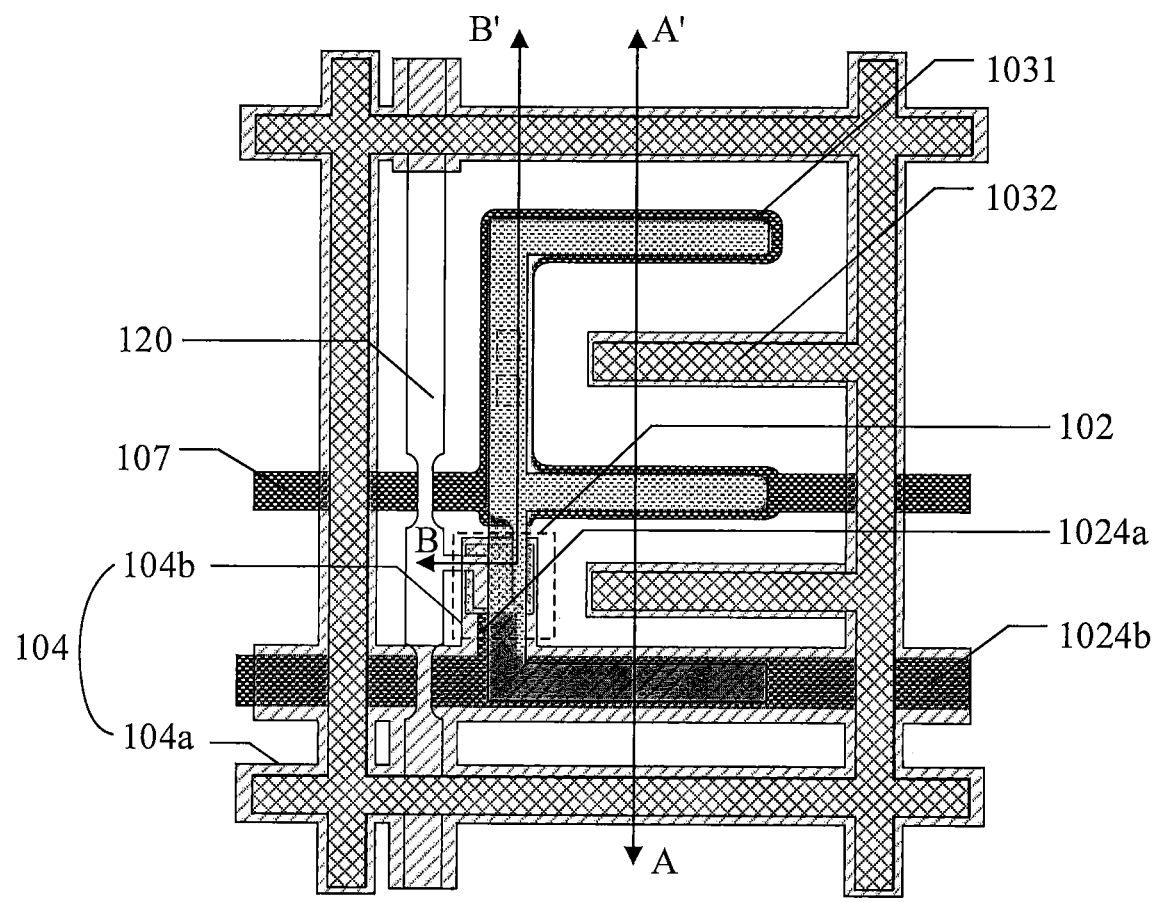
FIG. 1 is a schematic partial plan view of a ray detector according to an embodiment of the present disclosure.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

Spatially relative terms, such as "beneath", "below", "lower", "under", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of "above" and "below". Terms such as "before" or "preceding" and "after" or "followed by" may be similarly used, for example, to indicate an order in which light passes through the elements. The device may be otherwise oriented (rotated 90 degrees or at other orientations) and the spatially relative descriptors used herein may be interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It will be understood that when an element or layer is referred to as being "on", "connected to", "coupled to", or "adjacent to" another element or layer, it can be directly on, connected, coupled, or adjacent to the other element or layer, or intervening elements or layers may be present. In contrast, when an element is referred to as being "directly on," "directly connected to", "directly coupled to", or "directly adjacent to" another element or layer, there are no intervening elements or layers present. In no event, however, should "on" or "directly on" be construed as requiring a layer to completely cover an underlying layer.

Embodiments of the disclosure are described herein with reference to schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of the disclosure.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

To make the objectives, technical solutions, and advantages of the present disclosure clearer, the embodiments of the present disclosure will be described in further detail below with reference to the accompanying drawings.

Due to its specific structure, a conventional MSM photodiode usually suffers from interference generated in its interior, resulting in poor electrical performance of the MSM photodiode, which affects the accuracy of the ray detector. In view of this, embodiments of the present disclosure advantageously provide some options for improved accuracy of the ray detector.

Figure 3:
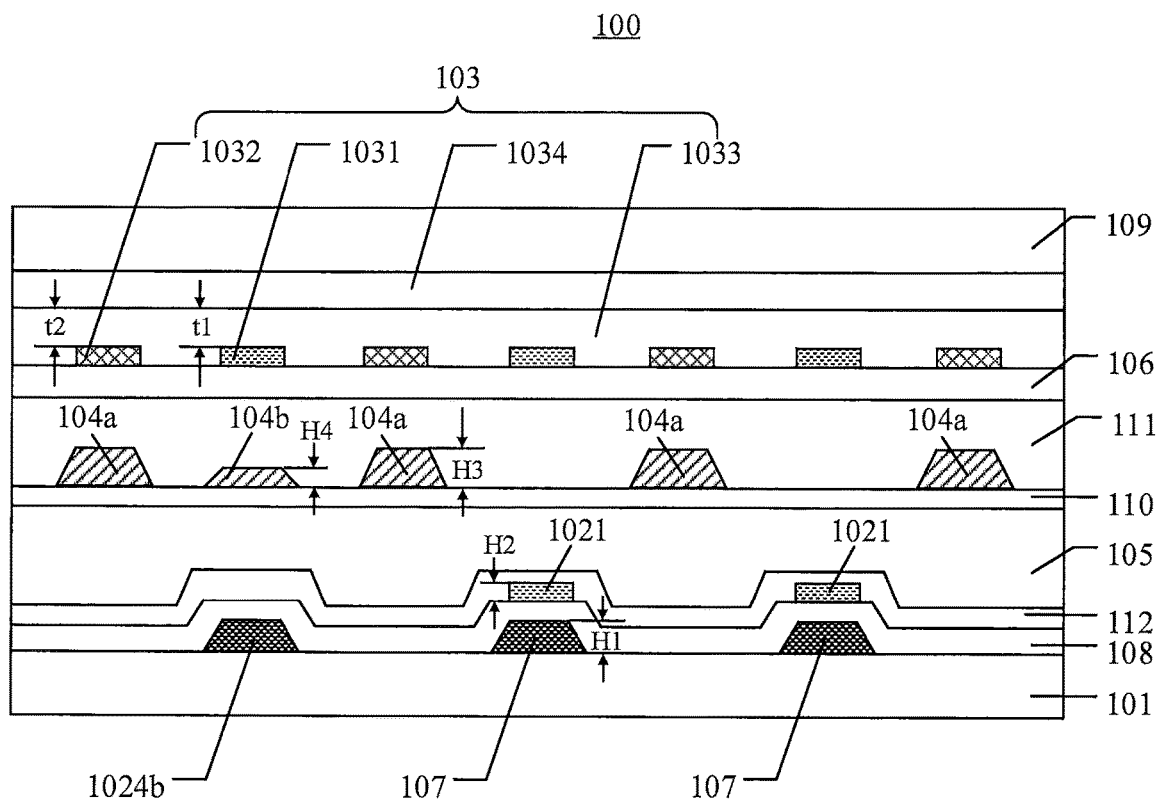
FIG. 3 is a schematic partial cross-sectional view of the ray detector taken along line A-A' in FIG. 1.
Figure 4:
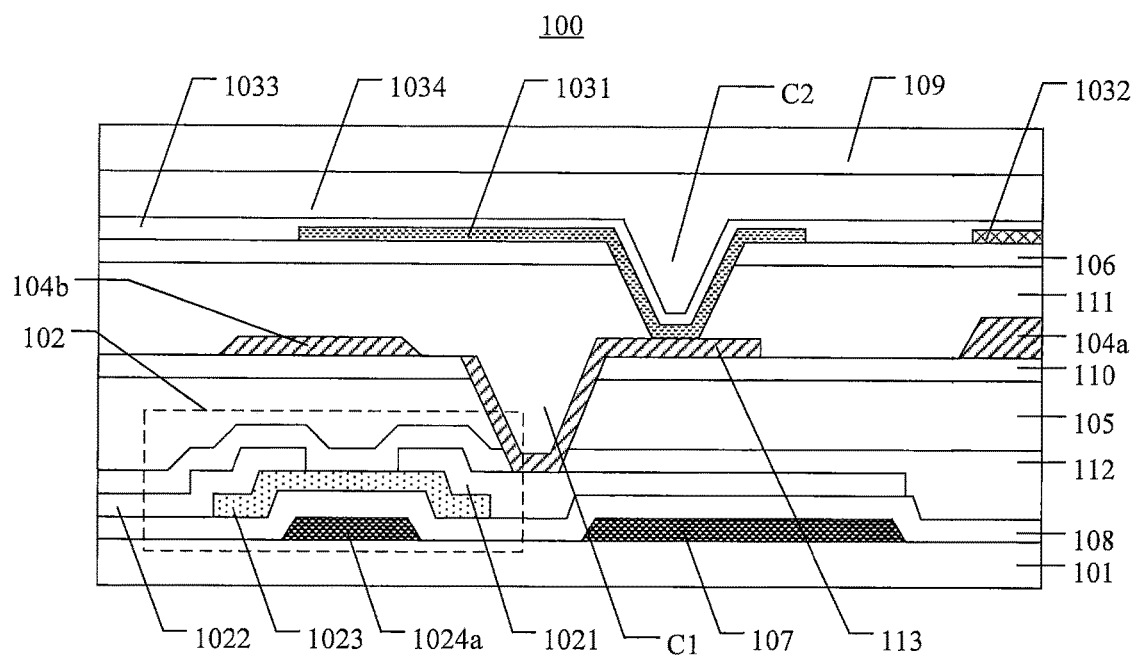
FIG. 4 is a schematic partial cross-sectional view of the ray detector taken along line B-B' in FIG. 1.

FIG. 1 is a schematic partial plan view of a ray detector according to an embodiment of the present disclosure, FIG. 3 is a schematic partial cross-sectional view of the ray detector taken along line A-A' in FIG. 1, and FIG. 4 is a schematic partial cross-sectional view of the ray detector taken along line B-B' in FIG. 1. For clarity, some elements may have been omitted from these figures.

Referring to FIGS. 1, 3 and 4, the ray detector 100 includes a base substrate 101. The base substrate 101 may be made of, for example, glass, quartz, plastic, or other suitable materials, which is not limited in the present disclosure. A plurality of pixel regions are arranged in an array on the base substrate 101, although only one of them is shown in the figure. Each pixel region includes a thin film transistor 102 and a photoelectric sensor 103 on the thin film transistor 102.

The thin film transistor 102 includes a structure such as a drain 1021 and a source 1022. As is known, the thin film transistor 102 is generally fabricated so that the drain 1021 and the source 1022 can be used interchangeably. Therefore, it will be understood that the drain 1021 may be referred to as a "source" in some cases, and the source 1022 may be referred to as a "drain" in some cases.

The thin film transistor 102 further includes a gate 1024a and a second semiconductor layer 1023. The gate 1024a is connected to the gate line 1024b. The second semiconductor layer 1023 and the gate 1024a are stacked on each other, and the second semiconductor layer 1023 is connected to the drain 1021 and the source 1022.

The photoelectric sensor 103 includes a first electrode 1031 and a second electrode 1032 spaced apart from each other, a dielectric layer 1033 on the first electrode 1031 and the second electrode 1032 and covering the first electrode 1031 and the second electrode 1032, and a first semiconductor layer 1034 on the dielectric layer 1033. As shown in FIG. 1, when viewed from above, the first electrode 1031 is patterned to be a comb-like structure. In this example, the first electrode 1031 has a shape similar to the letter "E". The second electrode 1032 is patterned to include a finger-like portion that forms an interdigital structure with the comb-like first electrode 1031 and a wiring portion that transmits a high voltage to the finger-like portion. The first electrode 1031 and the second electrode 1032 are spaced apart from each other, and the interval between them can be determined according to actual needs. As shown in FIG. 4, the first electrode 1031 is electrically connected to the drain 1021 of the thin film transistor 102 through a connection electrode 113, and the second electrode 1032 is electrically insulated from the thin film transistor 102. The dielectric layer 1033 can withstand a high voltage having a certain magnitude (for example, it may range from 200V to 400V). With a specific thickness (e.g., 100 nm to 200 nm), the electron tunneling of the dielectric layer 1033 occurs at a high electric field.

In this example, the photoelectric sensor 103 is an MSM photodiode, in which the dielectric layer 1033 is made of, for example, polyimide (PI), and the first electrode 1031 and the second electrode 1032 are made of, for example, aluminum, molybdenum, copper, or an alloy thereof, and the first semiconductor layer 1034 is made of, for example, amorphous silicon (a-Si).

It will be understood that, although not shown in the figures, the ray detector 100 also includes or works with a scintillator. The scintillator absorbs rays and converts radiant energy into light that can be detected by the photoelectric sensor 103. It should be noted that the scintillator can be selected to be sensitive to X-rays, γ-rays, or other rays according to actual needs. In this way, the ray detector 100 can function as a detector such as an X-ray detector, a γ-ray detector, or the like.

Figure 2:
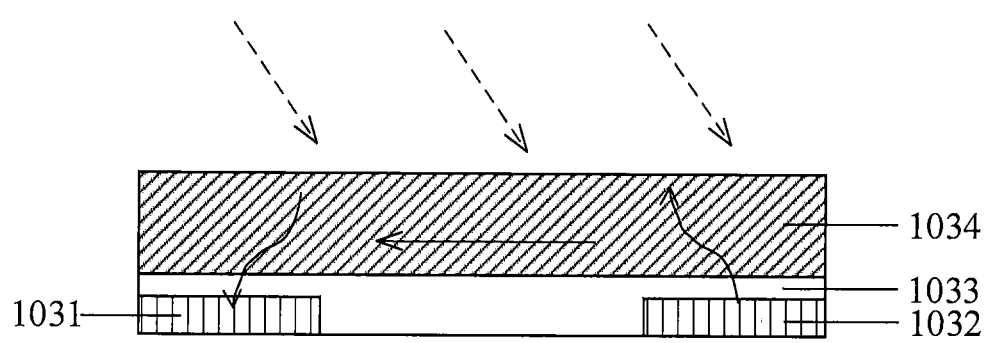
FIG. 2 is a schematic diagram of the working principle of an MSM photoelectric sensor according to an embodiment of the present disclosure.

FIG. 2 is a schematic diagram of the working principle of the MSM photoelectric sensor 103. Referring to FIG. 2, the second electrode 1032 is applied with a high voltage (e.g., 200V). When the surface of the first semiconductor layer 1034 is irradiated with no light, the first semiconductor layer 1034 has a high resistance, so that the high voltage is mainly distributed on the dielectric layer 1033 and the first semiconductor layer 1034. When the surface of the first semiconductor layer 1034 is irradiated with light (as shown by the dotted arrows in FIG. 2), the first semiconductor layer 1034 has a decreased resistance, and most of the high voltage is therefore distributed on the dielectric layer 1033. In this case, the second electrode 1032, the dielectric layer 1033, and the first semiconductor layer 1034 form a metal-insulator-semiconductor (MIS) structure. This MIS structure undergoes electron tunneling (i.e., Flower-Nordheim (FN)

tunneling) at a high voltage, resulting in a tunneling current (as shown by the solid arrows in FIG. 2). This tunneling current can be collected and read out for light detection.

Referring back to FIG. 1, FIG. 3, and FIG. 4, in an embodiment, a distance between the surface of the first electrode 1031 away from the base substrate 101 and the base substrate 101 is a first distance, and a distance between the surface of the second electrode 1032 away from the base substrate 101 and the base substrate 101 is a second distance, and the first distance and the second distance are substantially equal. Here, the phrase "the first distance and the second distance are substantially equal" means that the difference between the first distance and the second distance is less than a threshold. This threshold is selected so that the film layer formed on the first electrode 1031 and the second electrode 1032 can have a uniform thickness. That is, in the case of "the first distance and the second distance are substantially equal", the dielectric layer 1033 formed on the first electrode 1031 and the second electrode 1032 will have a good thickness uniformity and flatness. This allows the MSM photoelectric sensor 103 to have good electrical characteristics, thereby improving the accuracy of light detection.

The term "thickness" as used throughout this document refers to the thickness of the film layer in a direction perpendicular to the base substrate 101. In an embodiment, a portion of the dielectric layer 1033 at the surface of the first electrode 1031 away from the base substrate 101 (referred to as a first sub-dielectric layer for convenience of description) has a thickness t1, and a portion of the dielectric layer 1033 at the surface of the second electrode 1032 away from the base substrate 101 (referred to as a second sub-dielectric layer for convenience of description) has a thickness t2, where t1 and t2 are substantially equal. That is, the difference between the thickness t1 of the first sub-dielectric layer and the thickness t2 of the second sub-dielectric layer is less than a threshold. The threshold can be determined according to factors such as the electrical characteristics of the dielectric layer 1033 and the manufacturing process of the film layer. In some embodiments, the threshold may be selected such that the difference between the thickness t1 of the first sub-dielectric layer and the thickness t2 of the second sub-dielectric layer does not significantly affect the electrical characteristics of the photoelectric sensor 103. Exemplarily, the range of the threshold may be [−10%, 10%] of the thickness of the thinner one of the first and second sub-dielectric layers.

In some embodiments, the ray detector 100 further includes a first insulating layer 105 between the dielectric layer 1033 and the base substrate 101 and a second insulating layer 106 between the first insulating layer 105 and the dielectric layer 1033. The first insulating layer 105 and the second insulating layer 106 provide electrical isolation between the second electrode 1032 of the photoelectric sensor 103 and the thin film transistor 102.

With continued reference to FIGS. 1, 3 and 4, the ray detector 100 further includes a common electrode 107 and a shielding layer 104.

The common electrode 107 is provided between the base substrate 101 and the first insulating layer 105. In this example, the common electrode 107, the gate 1024a, and the gate line 1024b are in the same layer, and they can be formed through one patterning process, and thus have substantially the same thickness H1 ("first thickness"). An orthographic projection of the common electrode 107 on the base substrate 101 and an orthographic projection of the drain 1021 of the thin film transistor 102 on the base substrate 101 at least partially overlap. As shown in FIG. 1, in this example, the common electrode 107 is patterned to include a U-shaped portion that substantially overlaps the upper half of the E-shaped first electrode 1031 and a wiring portion that transmits a common voltage to the U-shaped portion. Similarly, although not explicitly shown in the figure, the drain 1021 of the thin film transistor 102 is also patterned to be a U-shaped structure that substantially overlaps the U-shaped portion of the common electrode 107. The U-shaped portion of the common electrode 107 and the U-shaped drain 1021 of the thin film transistor 102 form a storage capacitor. When the ray detector 100 is in operation, the common electrode 107 is applied with, for example, a ground voltage, and the drain 1021 of the thin film transistor 102 receives the tunneling current generated by the photodiode 103 via the connection electrode 113, so that the storage capacitor is charged by the tunneling current. The voltage across the storage capacitor is then transmitted as a sensing signal to the data line 120 via the thin film transistor 102 for reading.

The shielding layer 104 is between the first insulating layer 105 and the second insulating layer 106. The shielding layer 104 includes a first portion 104a and a second portion 104b. The first portion 104a covers the second electrode 1032 of the photoelectric sensor 103. Specifically, an orthographic projection of the first portion 104a on the base substrate 101 and an orthographic projection of the second electrode 1032 on the base substrate 101 at least partially overlap. In a specific example, the orthographic projection of the first portion 104a of the shielding layer 104 on the base substrate 101 covers the orthographic projection of the second electrode 1032 on the base substrate 101. The second portion 104b of the shielding layer 104 covers the channel region (and optionally, the gate line 1024b) of the thin film transistor 102. Specifically, an orthographic projection of the second portion 104b on the base substrate 101 covers at least an orthographic projection of the channel region of the thin film transistor 102 on the base substrate 101. The shielding layer 104 may be made of a light-shielding conductive material (e.g., aluminum, molybdenum, copper, or an alloy thereof). The material of the drain 1021 and the source 1022 of the thin film transistor 102 may be the same as that of the shielding layer 104.

In a specific embodiment, the orthographic projection of the first electrode 1031 on the base substrate 101 and the orthographic projection of the drain 1021 of the thin film transistor 102 on the base substrate 101 at least partially overlap, and the orthographic projection of the first electrode 1031 on the base substrate 101 and the orthographic projection of the common electrode 107 on the base substrate 101 at least partially overlap. That is, the common electrode 107 and the drain 1021 of the thin film transistor 102 are at least partially directly below the first electrode 1031. The orthographic projection of the first portion 104a of the shielding layer 104 on the base substrate 101 covers the orthographic projection of the second electrode 1032 of the photoelectric sensor 103 on the base substrate 101. That is, the first portion 104a of the shielding layer 104 is at least partially directly below the second electrode 1032 of the photoelectric sensor 103.

If the first distance between the surface of the first electrode 1031 away from the base substrate 101 and the base substrate 101 and the second distance between the surface of the second electrode 1032 away from the base substrate 101 and the base substrate 101 are greatly different, then when the dielectric layer 1033 is formed on the first electrode 1031 and the second electrode 1032, the portion of the dielectric layer 1033 above the first electrode 1031 (i.e., the first sub-dielectric layer) and the portion of the dielectric layer 1033 above the second electrode 1032 (i.e., the second sub-dielectric layer) will have a certain thickness difference (e.g., 1000 Å), resulting in the deteriorated electrical characteristics of the photoelectric sensor 103.

In view of this, in some embodiments, the shielding layer 104 is formed such that the thickness H3 ("third thickness") of the first portion 104a is substantially equal to a sum of the thickness H1 ("first thickness") of the common electrode 107 and the thickness H2 ("second thickness") of the drain 1021 of the thin film transistor 102. In this way, the first distance between the surface of the first electrode 1031 away from the base substrate 101 and the base substrate 101 and the second distance between the surface of the second electrode 1032 away from the base substrate 101 and the base substrate 101 can be substantially equal (in the case where the thickness of the first electrode 1031 and the thickness of the second electrode 1032 are substantially equal).

The following specifically describes how to achieve thickness uniformity of the dielectric layer 1033 on the first electrode 1031 and the second electrode 1032 by designing the thickness of the shielding layer 104.

As shown in FIGS. 3 and 4, between the first electrode 1031 and the base substrate 101, there are a common electrode 107, a gate insulating layer 108, a drain 1021 of the thin film transistor 102, a passivation layer 112, a first insulating layer 105, a first passivation layer 110, a second passivation layer 111, and the second insulating layer 106. Between the second electrode 1032 and the base substrate 101, there are a gate insulating layer 108, a passivation layer 112, a first insulating layer 105, a first passivation layer 110, a first portion 104a of the shielding layer 104, a second passivation layer 111 and a second insulating layer 106. It should be noted that, although not explicitly shown in the figures, each of the gate insulating layer 108, the passivation layer 112, the first insulating layer 105, the first passivation layer 110, the second passivation layer 111, and the second insulating layer 106 has a substantially uniform thickness throughout the base substrate 101, since each of them is an entire layer structure formed by one patterning process. Therefore, in the case where the thickness of the first electrode 1031 and the thickness of the second electrode 1032 are substantially the same, if the thickness H3 of the first portion 104a of the shielding layer 104 is substantially equal to the sum of the thickness H1 of the common electrode 107 and the thickness H2 of the drain 1021 of the thin film transistor 102, the first distance between the surface of the first electrode 1031 away from the base substrate 101 and the base substrate 101 can be substantially equal to the second distance between the surface of the second electrode 1032 away from the base substrate 101 and the base substrate 101. Therefore, the dielectric layer 1033 on the first electrode 1031 and the second electrode 1032 can have good thickness uniformity.

Here, "the thickness H3 of the first portion 104a of the shielding layer 104 is substantially equal to the sum of the thickness H1 of the common electrode 107 and the thickness H2 of the drain 1021 of the thin film transistor 102" includes the following two cases: (i) "the third thickness H3 of the first portion 104a of the shielding layer 104 is exactly equal to the sum of the first thickness H1 of the common electrode 107 and the second thickness H2 of the drain 1021 of the thin film transistor 102"; and (ii) "the third thickness H3 of the first portion 104a of the shielding layer 104 and the sum of the first thickness H1 of the common electrode 107 and the second thickness H2 of the drain 1021 of the thin film transistor 102 are slightly different. In either case, the first distance between the surface of the first electrode 1031 away from the base substrate 101 and the base substrate 101 and the second distance between the surface of the second electrode 1032 away from the base substrate 101 and the base substrate 101 are approximately equal. In this way, the segment difference between the surface of the first electrode 1031 away from the base substrate 101 and the surface of the second electrode 1032 away from the base substrate 101 is small, thereby allowing the thickness t1 of the portion of the dielectric layer 1033 above the first electrode 1031 (i.e., the first sub-dielectric layer) to be approximately equal to the thickness t2 of the portion of the dielectric layer 1033 above the second electrode 1032 (i.e., the second sub-dielectric layer) when the dielectric layer 1033 is formed.

In addition, the second portion 104b of the shielding layer 104 may have a thickness H4 ("fourth thickness"), which is substantially equal to the thickness H2 of the drain 1021 of the thin film transistor 102. As shown in FIGS. 3 and 4, since the gate line 1024b, the gate 1024a, and the common electrode 107 have approximately the same thickness H1, and the thickness H4 of the second portion 104b of the shielding layer 104 is substantially equal to the thickness H2 of the drain 1021 of the thin film transistor 102, the sum of the thickness of the gate line 1024b and the thickness H4 of the second portion 104b of the shielding layer 104 is substantially equal to the sum of the thickness H1 of the common electrode 107 and the thickness H2 of the drain 1021 of the thin film transistor 102. That is, the sum of the thickness of the gate line 1024b and the thickness H4 of the second portion 104b of the shielding layer 104 is substantially equal to the thickness H3 of the first portion 104a of the shielding layer 104. Therefore, the distance between the portion of the first electrode 1031 corresponding to the gate 1024a/gate line 1024b and the base substrate 101 is also substantially equal to the distance between the second electrode 1032 and the base substrate 101.

In one embodiment, the electrical signal applied on the shielding layer 104 may be the same as the common electrode signal (e.g., the ground voltage) applied on the common electrode 107. That is, the common electrode 107 and the shielding layer 104 are electrically connected to the same common voltage signal terminal. Of course, other embodiments are possible.

As described above, in order to achieve electron tunneling in the dielectric layer 1033, a high voltage (e.g., 200v) is usually applied to the second electrode 1032 of the photoelectric sensor 103. Compared to this high voltage, a sensing voltage across the storage capacitor (formed by the drain 1021 and the common electrode 107) generated by the tunneling current of the photoelectric sensor 103 is typically much smaller (e.g., 1V). In this way, a voltage difference of about 200V will be generated between the second electrode 1032 and the drain 1021 (or source 1022) of the thin film transistor 102, which has a strong interference on the sensing voltage. Due to the shielding effect of the shielding layer 104 (specifically, the first portion 104a), such interference caused by the high voltage applied to the second electrode 1032 can be reduced, thereby improving the accuracy of the sensing voltage.

In addition, the second semiconductor layer 1023 of the thin film transistor 102 may generate an undesired photo current under the irradiation of external light, resulting in a large off-state current of the thin film transistor 102. In some embodiments described above, since the orthographic projection of the second portion 104b of the shielding layer 104 on the base substrate 101 covers at least the orthographic projection of the channel region of the second semiconductor layer 1023 on the base substrate 101, it is possible to prevent external light from irradiating the second semiconductor layer 1023, thereby reducing the off-state current of the thin film transistor 102, and reducing the power consumption of the ray detector 100.

It should be noted that although the thin film transistor 102 shown in FIGS. 1, 3 and 4 is a bottom-gate structure, the structure of the thin film transistor 102 is not limited to this. In other embodiments, the thin film transistor 102 may be a top-gate structure.

In some embodiments, as shown in FIGS. 3 and 4, a first passivation layer 110 is disposed between the shielding layer 104 and the first insulating layer 105, and a second passivation layer 111 is disposed between the shielding layer 104 and the second insulating layer 106. This enhances the adhesion between the metal film layer and the insulating layer. The first passivation layer 110 and the second passivation layer 111 may be made of materials commonly used in the art, which is not limited in the present disclosure.

In addition, as shown in FIGS. 3 and 4, the ray detector 100 further includes a signal line layer 109 so as to apply an electric signal to each pixel region. By way of example, the signal line layer 109 is disposed on a side of the first semiconductor layer 1034 away from the base substrate 101. The signal line layer 109 may include a wiring (not shown) made of a transparent material such as indium tin oxide (ITO).

Figure 5:
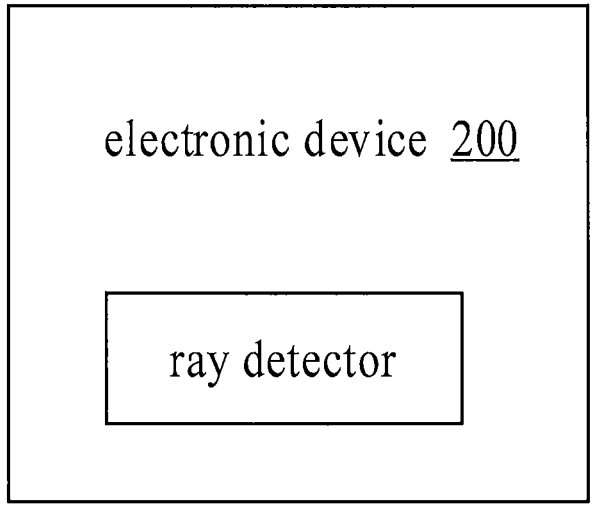
FIG. 5 is a schematic block diagram of an electronic device according to an embodiment of the present disclosure.

FIG. 5 is a schematic block diagram of an electronic device 200 according to an embodiment of the present disclosure. The electronic device 200 includes the ray detector described in any of the above embodiments. Examples of the electronic device 200 include, for example, medical diagnostic equipment, geological exploration equipment, and the like. The electronic device 200 has the same advantages as the above described embodiments of the ray detector, and for the sake of brevity, the description will not be repeated here.

Figure 6:
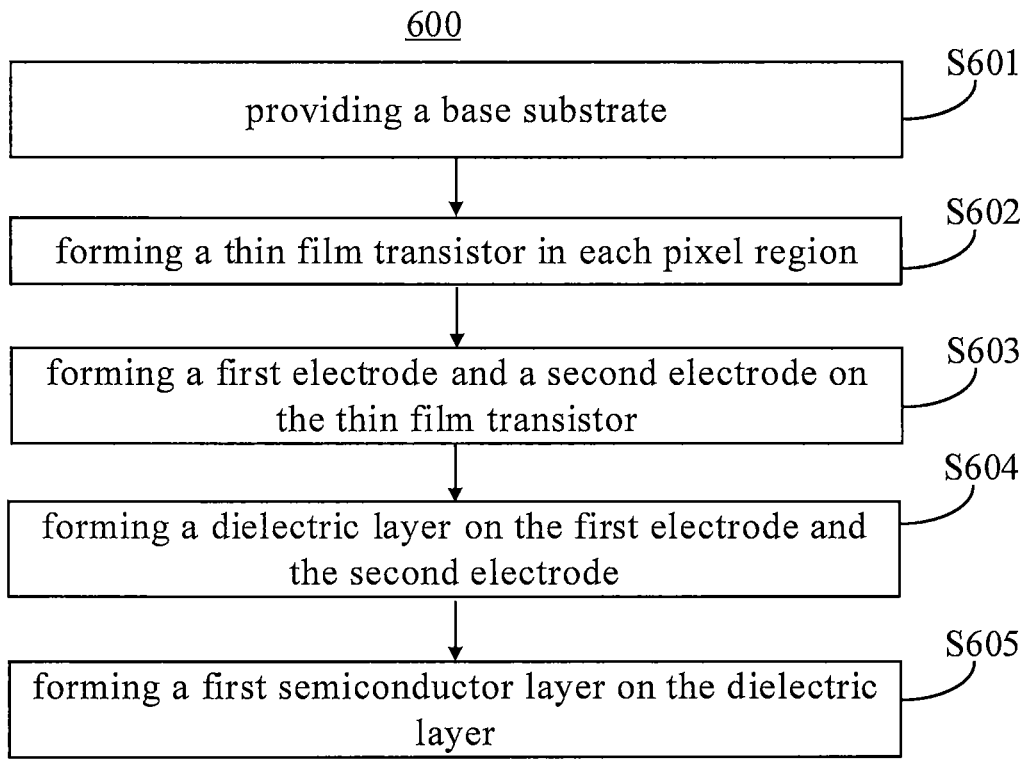
FIG. 6 is a flowchart of a method for manufacturing a ray detector according to an embodiment of the present disclosure.

FIG. 6 is a flowchart of a method 600 for manufacturing a ray detector according to an embodiment of the present disclosure. The method 600 may be applicable to the ray detector described in any one of the above embodiments. The method 600 is described below with reference to FIGS. 3, 4 and 6.

In step S601, a base substrate 101 is provided.

The base substrate 101 may be, for example, a glass substrate, a quartz substrate, a plastic substrate, or a substrate of other suitable materials, which is not limited in this disclosure. In an example, the base substrate 101 may be a flexible base substrate. A plurality of pixel regions are arranged in an array on the base substrate 101.

In step S602, a corresponding thin film transistor 102 is formed in each pixel region.

The thin film transistor 102 may be a top-gate thin film transistor or a bottom-gate thin film transistor. The process steps of forming the thin film transistor 102 are determined according to the type to which it belongs. For example, in an embodiment in which the thin film transistor 102 is a top-gate thin film transistor, step S602 may include: sequentially forming a drain 1021 and a source 1022, a second semiconductor layer 1023, a gate insulating layer 108, and a gate 1024a on the base substrate 101. In an embodiment in which the thin film transistor 102 is a bottom-gate thin film transistor (as shown in FIGS. 3 and 4), step S602 may include: sequentially forming a gate 1024a, a gate insulating layer 108, a second semiconductor layer 1023, and a drain 1021 and a source 1022 on the base substrate 101. In an example, the gate 1024a, the gate line 1024b and the common electrode 107 may be simultaneously formed on the base substrate 101 through one patterning process. The drain 1021 and the source 1022 can be used interchangeably according to the actual situation.

Taking the method of forming the second semiconductor layer 1023 as an example, the steps required to form the film layers in the thin film transistor 102 are described. A layer of semiconductor material with a certain thickness may be deposited on the base substrate 101 by a method such as magnetron sputtering, thermal evaporation, or plasma enhanced chemical vapor deposition (PECVD), to obtain the semiconductor material layer. Then, the semiconductor material layer is processed by a patterning process to obtain a second semiconductor layer 1023. The patterning process may include: photoresist coating, exposure, development, etching, and photoresist stripping. The semiconductor material may be materials such as amorphous silicon or polycrystalline silicon (P—Si). The thickness of the second semiconductor layer 1023 can be determined according to actual needs.

Subsequently, a passivation layer 112 is formed. A layer of passivation layer material with a certain thickness may be formed by a method such as deposition (such as chemical vapor deposition, physical vapor deposition) or coating, to obtain the passivation layer 112. The passivation layer 112 may be made of silicon dioxide, silicon nitride, or a mixed material of silicon dioxide and silicon nitride. The passivation layer 112 may be optional.

Then, a first insulating layer 105 is formed. For a method of forming the first insulating layer 105, reference may be made to the above-mentioned method of forming the passivation layer 112, and details are not described herein again. The first insulating layer 105 can be made of silicon dioxide, silicon nitride, or a mixed material of silicon dioxide and silicon nitride. The thickness of the first insulating layer 105 can be determined according to actual needs.

Next, a first passivation layer 110 is formed. For a method of forming the first passivation layer 110, reference may be made to the above-mentioned method of forming the passivation layer 112, and details are not described herein again. The first passivation layer 110 may be optional.

Subsequently, a first contact hole C1 penetrating the first passivation layer 110, the first insulating layer 105 and the passivation layer 112 is formed. The first contact hole C1 exposes a part of the drain 1021 of the thin film transistor 102.

Next, a shielding layer 104 and a connection electrode 113 are formed. A method such as magnetron sputtering, thermal evaporation, or PECVD may be used to deposit a layer of light-shielding and conductive material with a certain thickness on the first passivation layer 110 and in the first contact hole C1 to obtain a shielding material layer. The shielding material layer may be, for example, aluminum, molybdenum, copper, or an alloy thereof. Then, the shielding material layer is patterned by a patterning process to obtain the shielding layer 104 and the connection electrode 113. The formed shielding layer 104 includes a first portion 104a with a thickness H3 and a second portion 104b with a thickness H4. The first portion 104a and the second portion 104b with different thicknesses may be formed by halftone masking.

The orthographic projection of the second portion 104b of the shielding layer 104 on the base substrate covers at least the orthographic projection of the channel region of the second semiconductor layer 1023 of the thin film transistor 102 on the base substrate 101. In some embodiments, the orthographic projection of the second portion 104b of the shielding layer 104 on the base substrate also covers the orthographic projection of the gate line 1024b on the base substrate. In some embodiments, the thickness H3 of the first portion 104a of the shielding layer 104 is substantially equal to the sum of the thickness H1 of the common electrode 107 and the thickness H2 of the drain 1021 of the thin film transistor 102. In this way, it can facilitate the thickness uniformity of the dielectric layer 1033 to be formed.

Then, a second passivation layer 111 and a second insulating layer 106 are sequentially formed. For a method of forming the second passivation layer 111 and the second insulating layer 106, reference may be made to the above-mentioned method of forming the passivation layer 112, and details are not described herein. A second contact hole C2 is formed in the second passivation layer 111 and the second insulating layer 106. The second contact hole C2 exposes a part of the connection electrode 113.

In step S603, a first electrode 1031 and a second electrode 1032 are formed on the thin film transistor 102 in each pixel region.

A method such as magnetron sputtering, thermal evaporation, or PECVD can be used to deposit a layer of conductive material with a certain thickness on the second insulating layer 106 and in the second contact hole C2 to obtain an electrode material layer. Then, the electrode material layer is patterned by a patterning process to obtain a first electrode 1031 and a second electrode 1032. The first electrode 1031 and the second electrode 1032 are spaced apart from each other. In each pixel region, the first electrode 1031 is electrically connected to the drain 1021 of the thin film transistor 102 via the connection electrode 113 through the first contact hole C1 and the second contact hole C2, and the second electrode 1032 is electrically insulated from the thin film transistor 102 through the first insulating layer 105 and the second insulating layer 106. The orthographic projection of the second electrode 1032 on the base substrate 101 is covered by the orthographic projection of the first portion 104a of the shielding layer 104 on the base substrate 101.

The orthographic projection of the first electrode 1031 on the base substrate 101 and the orthographic projection of the drain 1021 of the thin film transistor 102 on the base substrate 101 at least partially overlap, and the orthographic projection of the first electrode 1031 on the base substrate 101 and the orthographic projection of the common electrode 107 on the base substrate 101 at least partially overlap. That is, the common electrode 107 and the drain 1021 of the thin film transistor 102 are at least partially below the first electrode 1031. The orthographic projection of the first portion 104a of the shielding layer 104 on the base substrate 101 covers the orthographic projection of the second electrode 1032 on the base substrate 101. Since the thickness H3 of the first portion 104a of the shielding layer 104 is substantially equal to the sum of the thickness H1 of the common electrode 107 and the thickness H2 of the drain 1021 of the thin film transistor 102, the first distance between the surface of the first electrode 1031 away from the base substrate 101 and the base substrate 101 is approximately equal to the second distance between the surface of the second electrode 1032 away from the base substrate 101 and the base substrate 101 (in the case where the thickness of the first electrode 1031 and the thickness of the second electrode 1032 are approximately equal).

In step S604, a dielectric layer 1033 is formed on the first electrode 1031 and the second electrode 1032 to cover the first electrode 1031 and the second electrode 1032.

A layer of dielectric material (e.g., polyimide) with a certain thickness may be formed on the base substrate 101 on which the first electrode 1031 and the second electrode 1032 are formed by a method such as deposition (e.g., chemical vapor deposition, physical vapor deposition) or coating, to obtain the dielectric layer 1033. Since the first distance between the surface of the first electrode 1031 away from the base substrate 101 and the base substrate 101 and the second distance between the surface of the second electrode 1032 away from the base substrate 101 and the base substrate 101 are approximately equal, the dielectric layer 1033 on the first electrode 1031 and the second electrode 1032 has good thickness uniformity. That is, the thickness t1 of the portion of the dielectric layer 1033 above the first electrode 1031 and the thickness t2 of the portion of the dielectric layer 1033 above the second electrode 1032 are substantially equal.

In step S605, a first semiconductor layer 1034 is formed on the dielectric layer 1033.

For a method of forming the first semiconductor layer 1034, reference may be made to the above-mentioned method of forming the second semiconductor layer 1023, and details are not described herein again. The first electrode 1031, the second electrode 1032, the dielectric layer 1033, and the first semiconductor layer 1034 form the photoelectric sensor 103 of the ray detector.

The method 600 for manufacturing a ray detector has the same advantages as the above described embodiments of the ray detector, and for the sake of brevity, the description will not be repeated here.

It should be noted that the above-mentioned embodiments illustrate rather than limit the disclosure, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in the claim. The article "a" or "an" preceding an element does not exclude the presence of a plurality of such elements. The mere fact that certain measures are recited in mutually different dependent claims does not indicate that a combination of these measures cannot be used to advantage.

The invention claimed is:

1. A ray detector comprising:
   a base substrate comprising a plurality of pixel regions arranged in an array, wherein each pixel region of the plurality of pixel regions comprises:
   a thin film transistor comprising a source and a drain; and
   a photoelectric sensor on a side of the thin film transistor away from the base substrate, wherein the photoelectric sensor comprises:
   a first electrode and a second electrode spaced apart from each other;
   a dielectric layer on a side of the first electrode and a side of the second electrode that are away from the base substrate, wherein the dielectric layer overlaps the first electrode and the second electrode; and
   a first semiconductor layer on a side of the dielectric layer away from the base substrate,
   wherein the first electrode is electrically connected to the drain,
   wherein a distance between a surface of the first electrode away from the base substrate and the base substrate is a first distance,
   wherein a distance between a surface of the second electrode away from the base substrate and the base substrate is a second distance, and wherein the first distance is substantially equal to the second distance.

2. The ray detector according to claim 1, further comprising:
a first insulating layer between the dielectric layer and the base substrate;
a second insulating layer between the first insulating layer and the dielectric layer; and
a shielding layer between the first insulating layer and the second insulating layer,
wherein the shielding layer comprises a first portion, and
wherein an orthographic projection of the first portion on the base substrate and an orthographic projection of the second electrode on the base substrate at least partially overlap.

3. The ray detector according to claim 2, wherein the orthographic projection of the first portion of the shielding layer on the base substrate covers the orthographic projection of the second electrode on the base substrate.

4. The ray detector according to claim 2, further comprising:
a common electrode between the base substrate and the first insulating layer,
wherein orthographic projections of the first electrode, the drain, and the common electrode on the base substrate at least partially overlap with each other.

5. The ray detector according to claim 4,
wherein the common electrode comprises a first thickness, the drain comprises a second thickness, and the first portion of the shielding layer comprises a third thickness, and
wherein the third thickness is substantially equal to a sum of the first thickness and the second thickness.

6. The ray detector according to claim 5,
wherein the thin film transistor further comprises a gate and a second semiconductor layer stacked on each other,
wherein the gate is between the base substrate and the first insulating layer,
wherein the second semiconductor layer is connected to the source and the drain,
wherein a portion of the second semiconductor layer between the source and the drain forms a channel region,
wherein the shielding layer further comprises a second portion, and
wherein an orthographic projection of the second portion on the base substrate overlaps at least an orthographic projection of the channel region on the base substrate.

7. The ray detector according to claim 6,
wherein orthographic projections of the first electrode, the second portion of the shielding layer, and the gate on the base substrate at least partially overlap with each other,
wherein the gate comprises a fifth thickness substantially equal to the first thickness, and
wherein the second portion of the shielding layer comprises a fourth thickness, and the fourth thickness is substantially equal to the second thickness.

8. The ray detector according to claim 7, further comprising:
a gate line between the base substrate and the first insulating layer and connected to the gate,
wherein orthographic projections of the first electrode, the second portion of the shielding layer, and the gate line on the base substrate at least partially overlap with each other, and
wherein the gate line comprises the fifth thickness substantially equal to the first thickness.

9. The ray detector according to claim 4, wherein the common electrode and the shielding layer are electrically connected to a same common voltage signal terminal.

10. An electronic device comprising the ray detector according to claim 1.

11. A method for manufacturing a ray detector, comprising:
providing a base substrate comprising a plurality of pixel regions arranged in an array;
forming a corresponding thin film transistor in each pixel region of the plurality of pixel regions, wherein the thin film transistor comprises a source and a drain;
forming a first electrode and a second electrode on a side of the thin film transistor in each pixel region away from the base substrate, wherein the first electrode and the second electrode are spaced apart from each other, and the first electrode is electrically connected to the drain;
forming a dielectric layer overlapping the first electrode and the second electrode on a side of the first electrode and a side of the second electrode that are away from the base substrate; and
forming a first semiconductor layer on a side of the dielectric layer away from the base substrate,
wherein the first electrode, the second electrode, the dielectric layer, and the first semiconductor layer form a photoelectric sensor,
wherein a distance between a surface of the first electrode away from the base substrate and the base substrate is a first distance,
wherein a distance between a surface of the second electrode away from the base substrate and the base substrate is a second distance, and
wherein the first distance is substantially equal to the second distance.

12. The method according to claim 11, further comprising:
before forming the first electrode and the second electrode, forming a first insulating layer on a side of the thin film transistor away from the base substrate;
forming a shielding layer on a side of the first insulating layer away from the base substrate; and
forming a second insulating layer on a side of the shielding layer away from the base substrate,
wherein the shielding layer comprises a first portion, and
wherein an orthographic projection of the first portion on the base substrate and an orthographic projection of the second electrode on the base substrate at least partially overlap.

13. The method according to claim 12, wherein the orthographic projection of the first portion of the shielding layer on the base substrate overlaps the orthographic projection of the second electrode on the base substrate.

14. The method according to claim 12, further comprising:
forming a common electrode between the base substrate and the first insulating layer,
wherein orthographic projections of the first electrode, the drain, and the common electrode on the base substrate at least partially overlap with each other.

15. The method according to claim 14,
wherein the common electrode comprises a first thickness, the drain comprises a second thickness, and the first portion of the shielding layer comprises a third thickness, and wherein the third thickness is substantially equal to a sum of the first thickness and the second thickness.

16. The method according to claim 15,
wherein forming the corresponding thin film transistor in each pixel region comprises forming a gate and a second semiconductor layer stacked on each other, wherein the gate is between the base substrate and the first insulating layer, wherein the second semiconductor layer is connected to the source and the drain, and wherein a portion of the second semiconductor layer between the source and the drain forms a channel region, and
wherein forming the shielding layer comprises forming a second portion of the shielding layer, wherein an orthographic projection of the second portion on the base substrate overlaps at least an orthographic projection of the channel region on the base substrate.

17. The method according to claim 16,
wherein orthographic projections of the first electrode, the second portion of the shielding layer, and the gate on the base substrate at least partially overlap with each other,
wherein the gate comprises a fifth thickness substantially equal to the first thickness,
wherein the second portion of the shielding layer comprises a fourth thickness, and
wherein the fourth thickness is substantially equal to the second thickness.

18. The method according to claim 17, further comprising:
forming a gate line between the base substrate and the first insulating layer,
wherein the gate line is connected to the gate,
wherein orthographic projections of the first electrode, the second portion of the shielding layer, and the gate line on the base substrate at least partially overlap with each other, and
wherein the gate line comprises the fifth thickness substantially equal to the first thickness.

* * * * *